United States Patent [19]

Nachbur et al.

[11] 4,055,689
[45] Oct. 25, 1977

[54] PROCESS FOR FLAMEPROOFING ORGANIC FIBER MATERIAL

[75] Inventors: Hermann Nachbur, Dornach; Arthur Maeder, Therwill, both of Switzerland

[73] Assignee: Ciba-Geigy Corporation, Ardsley, N.Y.

[21] Appl. No.: 648,541

[22] Filed: Jan. 12, 1976

Related U.S. Application Data

[62] Division of Ser. No. 483,493, June 27, 1974, Pat. No. 3,946,092.

[30] Foreign Application Priority Data

July 3, 1973 Switzerland .......................... 9671/73

[51] Int. Cl.² .......................... C09K 3/28; C09D 5/18
[52] U.S. Cl. ............................... 427/379; 106/15 FP; 252/8.1; 427/381; 427/389; 427/390 D; 428/270; 428/272; 428/277; 428/921
[58] Field of Search ................... 427/390 D, 394, 379, 427/381, 389; 428/276, 270, 277, 272, 921; 106/15 FP; 252/8.1; 260/964

[56] References Cited

U.S. PATENT DOCUMENTS

| | | | |
|---|---|---|---|
| 3,706,821 | 12/1972 | Anderson et al. | 260/964 X |
| 3,783,016 | 1/1974 | Randall et al. | 252/8.1 X |
| 3,927,231 | 12/1975 | Desitter et al. | 427/390 D |

OTHER PUBLICATIONS

Houben–Weyl, *Methoden der Organischen Chemie*, vol. 12/2 (1964), p. 327.

*Primary Examiner* — Harry J. Gwinnell
*Attorney, Agent, or Firm* — Edward McC. Roberts; Prabodh I. Almaula

[57] ABSTRACT

Process for flameproofing organic material, which comprises applying to said material a preparation containing a phosphate of the formula

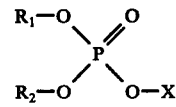

wherein X is phenyl or substituted phenyl, $R_1$ and $R_2$ each is bromoalkylene, then drying the material and subjecting it to heat treatment.

15 Claims, No Drawings

PROCESS FOR FLAMEPROOFING ORGANIC FIBER MATERIAL

This is a division of application Ser. No. 483,493 filed on June 27, 1974, now U.S. Pat. No. 3,946,092, The invention provides phosphates of the formula

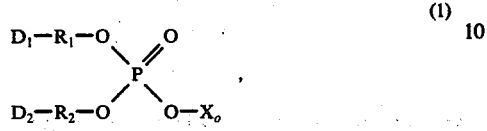
(1)

wherein $X_o$ represents unsubstituted phenyl, phenyl which is substituted in ortho- or para-position by phenyl, monoalkylphenyl or dialkylphenyl with 1 to 9 carbon atoms in each alkyl moiety, or represents a radical of the formula

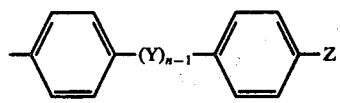
(1.1)

in which Y represents oxygen, methylene or isopropylidene, n is 1 or 2 and Z represents hydrogen, hydroxyl or a radical of the formula

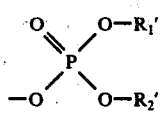
(1.2)

each of $R_1$, $R_2$, $R_1'$ and $R_2'$ represents alkylene with 2 to 6, preferably 3, carbon atoms which is substituted by at least one bromine atom and optionally by chlorine or hydroxyl, each of $D_1$ and $D_2$ represents hydrogen, hydroxyl or bromine or $D_1$ and $D_2$ together represent a radical of the formula

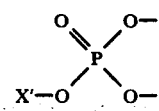
(1.3)

or at most one of the radicals $D_1$ and $D_2$ represents a radical of the formula

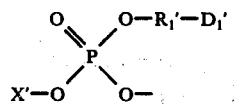
(1.4)

wherein $X'$ and $D_1'$ have the meanings assigned to $X$ and $D_1$, and, if $D_1$ and $D_2$ represent radicals of the formulae (1.3) or (1.4), Z is hydrogen or hydroxyl.

Preferred phosphates have the formula

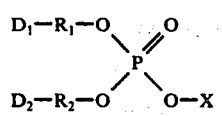
(2)

wherein $D_1$, $D_2$, $R_1$ and $R_2$ have the meanings assigned to them and X represents phenyl, monoalkylphenyl or dialkylphenyl with 1 to 9 carbon atoms in each alkyl moiety, or represents a radical of the formula (1.1).

The phosphates of the formula (1) or (2) can basicall be of four different types which are always built up on the same basic skeleton and which can be represented thus:

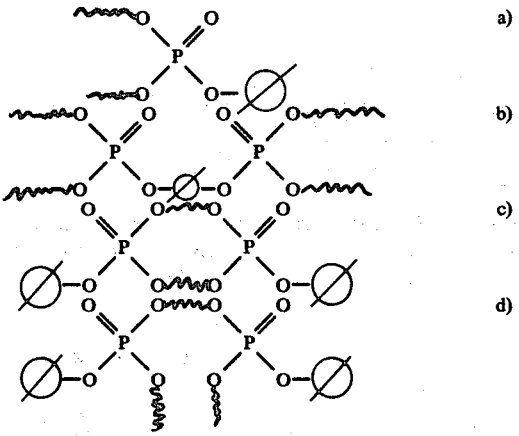

Type (a), the monophosphate, is preferred. Type (b) consists of 2 phosphates bound through the aromatic radical and the least preferred types (c) and (d) are 2 phosphates bound through the bromoalkyl radical $R_1$ or $R_2$.

The radicals $R_1$, $R_2$, $R_1'$ and $R_2'$ in the formulae (1), (1.2), (1.4) and (2) can be the same or not the same. Preferably, all four radicals have the same meaning. $R_1$, $R_2$, $R_1'$ and $R_2'$ preferably represent a bromoalkyl radical with 2 to 6, in particular 3, carbon atoms and 1 to 4, in particular 1 to 3, bromine atoms. As examples of such radicals there may be mentioned: 2-bromoethyl, 3-bromo-n-propyl, 2,2,3,3-tetrabromo-n-propyl, 2,2,3-tribromo-n-propyl, 2-chloro-2,3-dibromo-n-propyl or, above all, 2,3-dibromo-n-propyl. Mention may also be made of 2-chloro-3-bromo-n-propyl, 3-hydroxy-2-bis-(bromomethyl)-n-propyl, dibromoneopentyl or especially tribromoneopentyl.

Particularly interesting phosphates are those of the formula

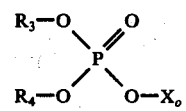
(3)

wherein each of $R_3$ and $R_4$ represents bromoalkyl with 2 to 5 carbon atoms and $X_o$ represents unsubstituted phenyl, phenyl substituted in ortho- or para-position by phenyl, monoalkylphenyl or dialkylphenyl with 1 to 9 carbon atoms in each alkyl moiety, or represents a radical of the formula (1.1), or especially phosphates of the formula

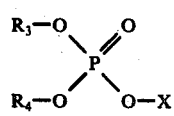
(4)

wherein each of $R_3$ and $R_4$ represent bromoalkyl with 2 to 5 carbon atoms and X represents phenyl, monoalkylphenyl or dialkylphenyl with 1 to 9 carbon atoms in each alkyl moiety, or represents a radical of the formula (1.1).

Useful phosphates are those of one of the formulae (1), (2) or (3), wherein $X_o$ represents phenyl which is substituted in ortho- or para-position by phenyl.

Of preeminent interest are chiefly phosphates of the formula

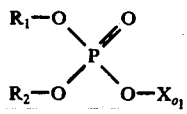
(5)

wherein $X_o$ represents phenyl, alkylphenyl with 1 to 9 carbon atoms in the alkyl moiety, 2- or 4-diphenylyl, or represents a radical of the formula

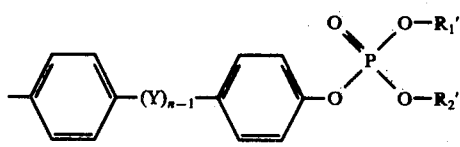
(5.1)

and $R_1$, $R_2$, $R_1'$, $R_2'$, Y and n have the meanings previously assigned to them, and, in particular, phosphates of the formula

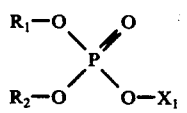
(6)

wherein $X_1$ represents phenyl, alkylphenyl with 1 to 9 carbon atoms in the alkyl moiety, 4-diphenylyl, or represents a radical of the formula (5.1) and $R_1$, $R_2$, $R_1'$, $R_2'$, Y and n have the meanings previously assigned to them.

Particularly suitable phosphates are those of the formula

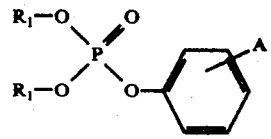
(7)

wherein A represents hydrogen or alkyl with 1 to 9 carbon atoms and $R_1$ has the meaning previously assigned to it.

Phosphates which have proved to be particularly useful are those of the formula

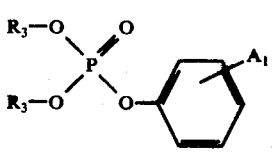
(8)

or especially those of the formula

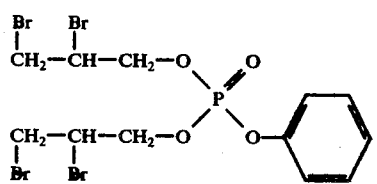
(9)

wherein $R_3$ represents dibromopropyl and $A_1$ represents hydrogen or methyl.

Other interesting phosphates are those of the following formulae:

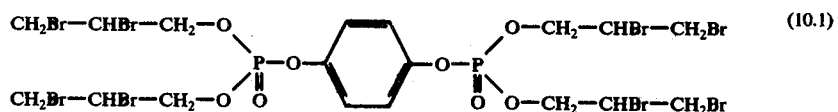
(10.1)

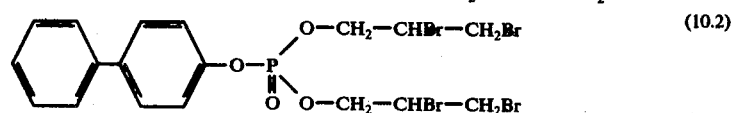
(10.2)

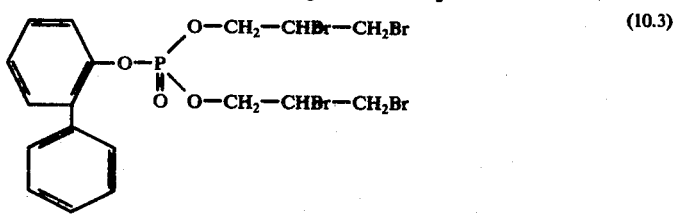
(10.3)

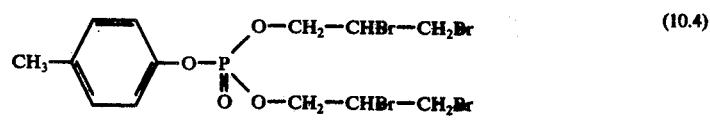
(10.4)

-continued

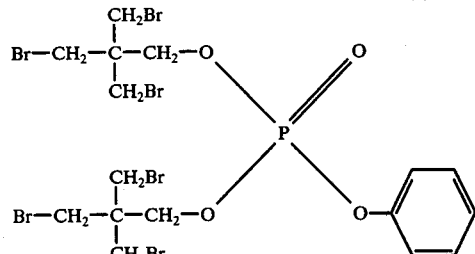 (10.5)

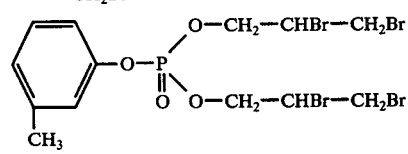 (10.6)

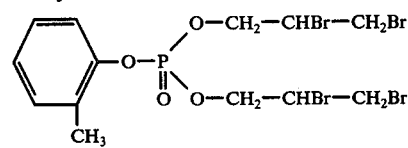 (10.7)

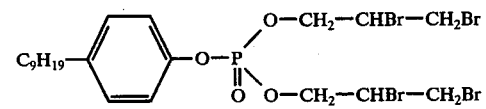 (10.8)

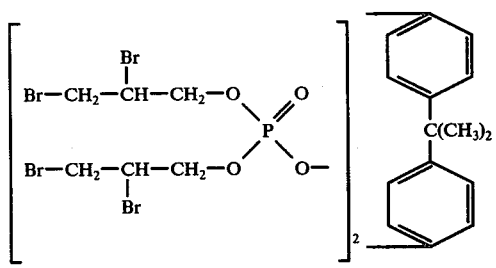 (10.9)

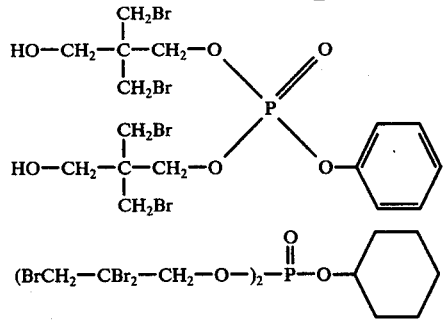 (10.10)

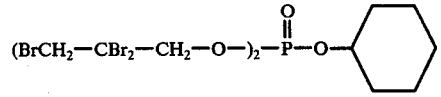 (10.11)

Of these, the most preferred phosphates are those of the formulae (10.1) and, above all, (10.2) to (10.7).

The phosphates of the formula (1) are manufactured by methods which are known per se and the process consists in esterifying a phosphoric acid dihalide of the formula

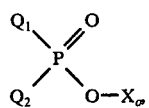 (11)

wherein each of the symbols $Q_1$ and $Q_2$ represents chlorine or bromine and $X_o$ has the meaning previously assigned to it, with at least one brominated alkanol of the formula $R_1$ — OH    (12)

wherein $R_1$ has the meaning previously assigned to it, or with an alkenol with 2 to 6 carbon atoms, in which latter case, if hydrogen halide has been added during the esterification, bromine is added to the double bond after hydrogen chloride has been split off.

The manufacture of the phosphates of the formula (2) proceeds in analogous manner by esterifying a phosphoric acid dihalide of the formula

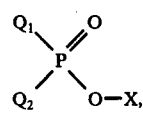 (13)

wherein $Q_1$, $Q_2$ and X have the meanings previously assigned to them, with at least one brominated alkanol of the formula (12), or with an alkenol with 1 to 6 carbon atoms, in which latter case, after any hydrogen chloride which may have been added to the double bond during the esterification has been split off, the double bond is further reacted with bromine.

The starting products of the formula (11) or (13) are also manufactured by known methods by e.g. reacting 1 mole of an appropriate phenol or of an appropriate phenol derivative with surplus phosphoroxy halide (e.g. 6 moles) to give the corresponding arylphosphoric acid dihalide. Esterification can then be effected with the appropriate brominated alkanol, e.g. 2,3-dibromopropanol, to yield a phosphate according to the invention of the formula (1). Another means consists in carrying out the reaction with e.g. allyl alcohol or propargyl alcohol or, above all, 2-chloroallyl alcohol, 3-chloroallyl alcohol or 2-bromoallyl alcohol, splitting off any hydrogen chloride which has been added to the unsaturated group, and brominating the now free allyl group.

As phosphoric acid dihalides there are preferably used the corresponding dichlorides. Particularly suitable dichlorides are those of the formula

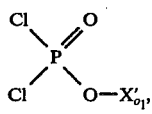

(14)

wherein $X_{o_1'}$ represents unsubstituted phenyl, phenyl which is substituted in ortho- or para-position by phenyl, monoalkylphenyl or dialkylphenyl with 1 to 9 carbon atoms in each alkyl moiety, or represents a radical of the formula

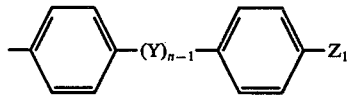

(14.1)

wherein Y and n have the meanings previously assigned to them and $Z_1$ represents hydrogen or hydroxyl, or especially dichlorides of the formula

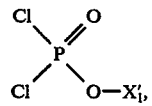

(15)

wherein $X_1'$ represents phenyl, monoalkyl- or dialkylphenyl with 1 to 9 carbon atoms in each alkyl moiety, or represents a radical of the formula (14.1), in which Y, $Z_1$ and n have the meanings previously assigned to them.

Preferred dichlorides are also, for example, those of the formula

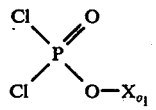

(16)

wherein $X_{o_1}$ has the meaning previously assigned to it, but preferably represents here alkylphenyl with 1 to 9, in particular 1 to 4 carbon atoms in the alkyl moiety, 2- or 4-diphenylyl or, above all, phenyl, or especially those of the formula

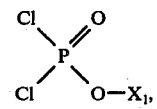

(17)

wherein $X_1$ has the meaning previously assigned to it. Preferably, however, $X_1$ represents here alkylphenyl with 1 to 9, in particular 1 to 4, carbon atoms in the alkyl moiety or above all represents phenyl.

Ordinarily, 1 mole, optionally 1.5 moles, of alcohol is used for each halogen in the phosphoric acid halide.

Optionally, the esterification of the phosphoric acid chloride is carried out in the presence of an acid acceptor, e.g. pyridine or triethylamine.

The phosphates according to the invention are used primarily for flameproofing organic material, in particular organic fibre material such as polyester fibres.

The method of flameproofing organic material consists in applying to this material a preparation which contains at least one compound according to any one of the formulae (1) to (7), drying the material and subjected it to a heat treatment at 175° C to 220° C, preferably at 190° C to 210° C. The preparations or agents which are used for flameproofing the material can be in the form of aqueous emulsions or suspensions or organic solutions.

Suitable solvents are aliphatic alcohols, ketones or esters with at most 4 carbon atoms, also aromatic or cycloaliphatic hydrocarbons with 1 to 7, in particular 1 to 4, carbon atoms, e.g. methanol, ethanol, isopropanol, n-butanol, tert.butanol, acetone, methyl ethyl ketone, methyl isobutyl ketone, butyrolacetone, dioxan, tetrahydrofuran, benzene, toluene, chloroform, dichloroethane, trichloroethane, carbon tetrachloride, ethylene glycol monoethyl ether. Particularly good results are obtained with the aliphatic alcohols, e.g. ethanol or methanol, or with the chlorinated hydrocarbons, e.g. trichloroethylene.

If desired, it is also possible to apply the phosphates of the formula (1) as aqueous emulsions. Desirably, the procedure to be followed here is that the phosphate is dissolved first in an organic, water-insoluble solvent such as benzene or toluene and the resulting solution is then emulsified in water by vigorous stirring. Alternatively, it is also possible to emulsify the phosphate direct in a concentrated emulsifier solution and then to prepare an emulsion of the desired concentration by dilution with water.

Depending on the desired coating, the preparations for finishing the textiles contain 5 to 25, preferably 10 to 25 and in particular 10 to 20, precent by weight of the compound of the formula (1). The preparations which contain the compounds of the formula (1) can be applied to the material by conventional methods by spraying, padding, exhaustion or printing. Preferably the preparations are applied by the padding method.

After the phosphates of the formula (1) have been applied, the material is dried, preferably at temperatures below 100° C, e.g. at 70° C to 100° C, and then subjected to a thermosol process at 175° C to 220° C. This thermosol process generally lasts about 10 to 200 seconds, preferably 20 to 100 seconds and especially 20 to 60 seconds.

The polyester fibres are preferably those derived from terephthalic acid, e.g. poly(ethylene glycol terephthalate) or poly(1,4-cyclohexylenedimethyleneterephthalate). Polyester and copolyester fibres which can be treated effectively with the products according to the invention are descrined e.g. in U.S. Pat. Nos. 2,465,319 or 2,901,466.

But besides polyester fibres it is also possible to use other fibres, e.g. synthetic polyamide fibres or wool fibres or those made from regenerated cellulose, cellulose diacetate or triacetate; fibre blends are also suitable. However, synthetic fibre materials are preferred, above all textile. The materials can be in the form of threads, flocks, non-wovens, woven or knitted fabrics, the two last mentioned being preferred.

The phosphates according to the invention of the formula (1) effect on organic textile materials, especially those made from polyester fibres, permanent flameproof finishes which have the added advantage that the handle of the finished materials does not have an oily feel as can happen when known agents are used. The flameproofing effects are also retained after several washes or dry cleanings.

In addition to the textile application, the phosphates according to the invention can also be used as flame retardants in other kinds of application, i.e. as additives to plastics, for example:
polystyrene moulding compounds
polyester systems
polyurethane foams
epoxide resin compositions
polyvinyl chloride systems
paper together with a suitable binder
varnish preparations
polyamide moulding compositions Parts and percentages in the following Examples are by weight unless indicated to the contrary, and the relationship between parts by weight and parts by volume is the same as that of the gram to the millilitre.

Manufacturing Directions

EXAMPLE 1

(bis-2,3-dibromopropyl)-phenylphosphate

A solution of 84.4 parts (0.4 mole) of phenylphosphoric acid dichloride in 100 parts by volume of dry benzene is added dropwise over the course of 30 minutes to an ice cold (0° C to 1° O) solution of 174.4 parts (0.8 mole) of 2,3-dibromopropyl alcohol and 63.2 parts of pyridine in 400 parts by volume of dry benzene. The mixture is subsequently stirred for 5 hours, in the course of which the temperature gradually rises to about 25° C. The pyridine hydrochloride which has formed is then isolated and the filtrate benzene phase is washed in succession with 1300 parts of water, then with 1300 parts of a 5% sodium carbonate solution and finally again with 1300 parts of water. The benzene phase is dried with anhydrous sodium sulphate, the benzene then removed therefrom and the residue is purified from unreacted starting materials by treatment in vacuo at 120° C/0.03–0.05 Torr. Yield: 192 parts (83 1/2% of theory) of a clear, colourless oil which corresponds to formula (9). The infrared spectrum shows the characteristic aromatic substance bands at 1580 and 1480 cm$^{-1}$, the P=O band at 1270 cm$^{-1}$, the P-O-aryl band at 1190 cm$^{-1}$, the P-O-alkyl band at 1030 cm$^{-1}$, and the 5 adjacent aromatic hydrogen atoms which are in positions 2,3,4,5 and 6 of the phenyl group at 760 cm$^{-1}$. In the mass spectrum the parent peak can be determined for the molecular weight 574. The indicated structural formula is clearly evident from the degradation products. The gel permeation chromatogram shows that the substance is homogeneous.

EXAMPLE 2

1,4-phenylene-[bis-(2,3-dibromopropyl-phosphate)]

A suspension of 68.6 parts (0.2 mole) of 1,4-phenylenephosphoryl dichloride in 300 parts by volume of acetonitrile is cooled to $-10°$ C and then treated over the course of 5 minutes with a solution of 63.2 parts (0.8 mole) of anhydrous pyridine in 100 parts by volume of acetonitrile. Then a solution of 174.4 parts (0.8 mole) of 2,3-dibromopropanol in 100 parts by volume of acetonitrile is added dropwise at 0° C to 10° C over the course of 30 minutes. The reaction mixture is subsequently kept for 1 hour at 0° C. The resulting clear solution is freed from acetonitrile in vacuo at 50° C to yield 315 parts of a white, greasy product which is stirred in 200 parts by volume of dried toluene using a homogenising device and cooled to $-5°$ C. The pyridine hydrochloride is filtered off and washed with 50 parts by volume of dried toluene. The toluene phase is concentrated in vacuo at about 100° C and the residue is freed from unreacted 2,3-dibromopropanol at 160° C and 14 Torr. Yield: 161 parts (75% of theory) of a viscous, brownish oil which corresponds to the formula (10.1). The infrared spectrum shows the characteristic aromatic substance bands at 1500 cm$^{-1}$, the P=O band at 1280 cm$^{-1}$, the P-O-aryl band at 1190 cm$^{-1}$, the P-O-alkyl band at 1050 cm$^{-1}$ and the two adjacent aromatic hydrogen atoms in positions 2, 3 and 5, 6 of the phenyl group at 840 cm$^{-1}$. The gel permeation chromatogram shows that the substance is homogeneous.

EXAMPLE 3 p-bisphenyl-(bis-2,3-dibromopropyl)-phosphate

A solution of 218 parts (1 mole) of 2,3-dibromopropyl alcohol in 100 parts by volume of dried toluene is cooled to $-10°$ C and treated over the course of 10 minutes with a solution of 79 parts (1 mole) of anhydrous pyridine in 50 parts by volume of toluene. A solution of 143.5 parts (0.5 mole) of phosphoric acid-p-biphenyl ester dichloride in 250 parts by volume of toluene is then added dropwise at $-10°$ C over the course of 45 minutes. The reaction mixture is subsequently kept for 2 hours at a temperature rising from $-10°$ C to 0° C. The precipitated pyridine hydrochloride is then filtered off and washed with 50 parts by volume of toluene. The toluene phase is washed twice with 200 parts by volume of water on each occasion, then once with 200 parts by volume of a 10% sodium carbonate solution and finally four times with 250 parts by volume of water on each occasion, after which the final washing is free of chloride. The toluene phase is finally concentrated in vacuo at about 100° C and the residue is freed from unreacted 2,3-dibromopropanol at 160° C and 14 Torr.

Yield: 224 parts (69% of theory) of a viscous, brownish oil which corresponds to the formula (10.2). The infrared spectrum shows the characteristic aromatic substance bands at 1600, 1505 and 1480 cm$^{-1}$, the P=O band at 1280 cm$^{-1}$, the P-O-aryl band at 1210 cm$^{-1}$, the P-O-alky at 1035 cm$^{-1}$, the two adjacent aromatic hydrogen atoms in 2,3 and 5,6 positions of the phenylene group at 840 cm$^{-1}$, and the 5 adjacent aromatic hydrogen atoms in positions 2,3,4,5,6 of the phenyl group at 760 cm$^{-1}$. The gel permeation chromatogram shows that the substance is homogeneous.

EXAMPLE 4

O-bisphenyl-(bis-2,3-dibromopropyl)-phosphate

The procedure as indicated in Example 3 is followed, except that phosphoric acid-o-biphenyl ester dichloride is used.

Yield: 301 parts (92 1/2% of theory) of a viscous, whitish grey product which corresponds to the formula (10.3).

The infrared spectrum shows the characteristic aromatic substance bands at 1570, 1490 and 1360 cm$^{-1}$, the P=O band at 1270 cm$^{-1}$, the P-O-aryl band at 1180 cm$^{-1}$, the P-O-alkyl band at 1030 cm$^{-1}$, the 4 adjacent aromatic hydrogen atoms in positions 3,4,5,6 of the phenylene group at 755 cm$^{-1}$, and the 5 adjacent aromatic hydrogen atoms in positions 2,3,4,5,6 of the phenyl group at 720 cm$^{-1}$. The gel permation chromatogram shows that the substance is homogeneous.

EXAMPLE 5 p-tolyl-(bis-2,3-dibromopropyl)-phosphate

The procedure as indicated in Example 3 is followed, except that 112.5 parts (0.5 mole) of phosphoric acid-p-tolyl ester dichloride are used.

Yield: 267 parts (91% of theory) of a clear, yellowish, viscous oil which corresponds to the formula (10.4). The infrared spectrum shows the characteristic aromatic substance bands at 1590 and 1485 cm$^{-1}$, the P=O band at 1280 cm$^{-1}$, the P-O-aryl band at 1200 cm$^{-1}$, the P-O-alkyl band at 1035 cm$^{-1}$, and the 2 adjacent aromatic hydrogen atoms in positions 2,3 and 5,6 of the phenylene group at 810 cm$^{-1}$. The gel permeation chromatogram shows that the substance is homogeneous.

EXAMPLE 6 phenyl-(bis-tribromoneopentyl)-phosphate

A solution of 325 parts of tribromoneopentyl alcohol (1 mole) in 250 parts by volume of dry toluene is cooled at −5° C, when a portion of the alcohol again precipitates. The suspension is treated at 0° C to −5° C over the course of 5 minutes with a solution of 79 parts of anhydrous pyridine (1 mole) in 50 parts by volume of toluene and a clear solution forms. To this solution is added dropwise over the course of 40 minutes a solution of 105.5 parts (0.5 mole) of phosphoric acid phenyl ester dichloride in 200 parts by volume of dry toluene at 0° C to −10° C. The reaction mixture is subsequently kept for 2 hours at about 0° C. The precipitated pyridine hydrochloride in then filtered off and washed with 50 parts by volume of toluene. The processing of the toluene phase is carried out as indicated in Example 3.

Yield: 270 parts (68 1/2% of theory) of a viscous, yellowish brown product which corresponds to the formula (10.5). The infrared spectrum shows the characteristic aromatic substance bands at 1580 and 1480 cm$^{-1}$, the P=O band at 1275 cm$^{-1}$, the P-O-aryl band at 1200 cm$^{-1}$, the P-O-alkyl band at 1020 cm$^{-1}$, and the 5 adjacent aromatic hydrogen atoms in positions 2,3,4,5,6 of the phenyl group at 760 cm$^{-1}$. The gel permeation chromatogram indicates that substantially the principal substance of the formula (10.5) is present.

EXAMPLE 7 m-tolyl-(bis-2,3-dibromopropyl)-phosphate

A solution of 174.5 parts of 2,3-dibromopropyl alcohol (0.8 mole) in 80 parts by volume of dry toluene is cooled to −10° C and treated at −5° C to −10° C with a solution of 63.2 parts of anhydrous pyridine (0.8 mole) in 50 parts by volume of toluene. Then a solution of 90 parts (0.4 mole) of phosphoric acid-m-tolyl ester dichloride in 160 parts by volume of toluene is added at −10° C to −15° C over the course of 70 minutes. The reaction mixture is subsequently kept for 2 hours at 0° C to −5° C. The precipitated pyridine hydrochloride is then filtered off and washed with 50 parts by volume of toluene. The processing of the toluene phase is carried out as indicated in Example 3.

Yield: 168 parts (71 ½% of theory) of a viscous, yellowish, clear oil which corresponds to the formula (10.6). The infrared spectrum shows the characteristic aromatic substance bands at 1600 and 1580 cm$^{-1}$, the P=O band at 1240 cm$^{-1}$ the P-O-alkyl band at 1045 cm$^{-1}$, the isolated aromatic hydrogen in position 2 of the phenylene group at 870 cm$^{-1}$, and the 3 adjacent aromatic hydrogen atoms in position 2,5,6 of the phenyl group at 780 cm$^{-1}$. The gel permeation chromatogram shows that the substance is homogeneous.

EXAMPLE 8 o-tolyl-(bis-2,3-dibromopropyl)-phosphate

The procedure as indicated in Example 3 is carried out, except that 112.5 parts (0.5 mole) of phosphoric acid-o-tolyl ester dichloride are used.

Yield: 263 parts (90% of theory) of a yellowish oil of medium viscosity which corresponds to the formula (10.7). The infrared spectrum shows the characteristic aromatic substance bands at 1580 and 1490 cm$^{-1}$, the P=O band at 1270 cm$^{-1}$, the P-O-aryl band at 1230 cm$^{-1}$, the P-O-alkyl band at 1040 cm$^{-1}$, and the 4 adjacent aromatic hydrogen atoms in positions 2,4,5,6 of the phenylene group at 760 cm$^{-1}$. The gel permeation chromatogram shows that the substance is homogeneous.

EXAMPLE 9 p-nonylphenyl-(bis-2,3-dibromopropyl)-phosphate

The procedure as indicated in Example 3 is carried out, except that 168.5 parts (0.5 mole) of phosphoric acid-p-nonylphenyl ester dichloride are used.

Yield: 320 parts (91 1/2% of theory) of a low viscosity, colourless oil which corresponds to the formula (10.8). The infrared spectrum shows the characteristic aromatic substance bands at 1600 and 1500 cm$^{-1}$, the P=O band at 1285 cm$^{-1}$, the P-O-aryl band at 1215 cm$^{-1}$, the P-O-alkyl band at 1045 cm$^{-1}$, and the 2 adjacent aromatic hydrogen atoms in positions 2,3 and 5,6 of the phenylene group at 840 cm$^{-1}$. The gel permeation chromatogram shows that the substance is homogeneous.

EXAMPLE 10 propane-2,2-[bis-(2,3-dibromopropyl)-phosphate]

The procedure as indicated in Example 3 is carried out, except that 115.5 parts (0.25 mole) of 2,2-[BIS-(4-dichlorophosphoryl-phenyl)]-propane are used.

Yield: 267 parts (90% of theory) of a viscous, opalescent oil which corresponds to the formula (10.9). The infrared spectrum shows the characteristic aromatic substance bands at 1600 and 1500 cm$^{-1}$, the P=O band at 1285 cm$^{-1}$, the P-O-aryl band at 1215 cm$^{-1}$, the P-O-alkyl band at 1045 cm$^{-1}$, and the 2 adjacent aromatic hydrogen atoms in the 2,3 and 5,6-positions of the two phenylene groups at 840 cm$^{-1}$. The gel permeation chromatogram shows that the substance is homogeneous.

Application Examples

EXAMPLE 11

A fabric of 100% polyester (polyethylene glycol terephthalate) weighing 150 g/m$^2$ is padded, dried, subjected to a thermosol treatment, washed, rinsed and dried in accordance with the particulars given in the following Table and tested for its flame resistance according to DOC FF 3-71. The washing is carried out over the course of 5 minutes at 40° C in a bath which contains 2 g/l of anhydrous sodium carbonate and 1 g/l of a condensation product of 1 mole of p-tert. nonylphenol and 9 moles of ethylene oxide. The flameproofing test is performed before and after the thermosol treatment and after 25 and 50 machine washes. The machine washes are carried out in a domestic washing machine at 40° C over the course of 45 minutes and in a liquor which contains 4 g/l of a household detergent. (SNV 158 861 Washing). The results are summarised in the following Table I:

Table I

| Constituents Conditions | un-treated | treated with liquor | | | |
|---|---|---|---|---|---|
| | | 1 | 2 | 3 | 4 |
| g of product of formula (9) per kg of liquor | 100 | 200 | 100 | 100 | |
| solvent | | tri-chloro-ethyl-ene | tri-chloro-ethyl-ene | tri-chloro-ethyl-ene | tri-chloro-ethyl-ene |
| liquor pick-up (%) | | 100 | 100 | 100 | 100 |
| thermosol treatment temperature in ° C | | 200 | 200 | 200 | 200 |
| thermosol treatment time | | 20 | 20 | 60 | 60 |
| deposit after final wash (%) | | 11.1 | 21 | 13 | 21 |
| Flame resistance (time: sec./tear length: cm) | | | | | |
| before thermosol treatment | 16/11 | 0/7.5 | 0/0.5 | 0/7.5 | 0/7 |
| after thermosol treatment | burns | 0/7 | 0/6.5 | 0/6 | 0/7 |
| after 25 washes | burns | 5/7.5 | 1/7.5 | 3/8 | 0/8 |
| after 50 washes | burns | 1/7 | 1/7 | 4/7.5 | 1/7 |

The above flameproofing test, DOC FF 3-71 ("Children's Sleepwear Test"), is carried out as follows: 5 pieces of fabric, each measuring 8.9 cm × 25.4 cm, are clamped into a testing frame and dried with circulating air for 30 minutes at 105° C in a drying cabinet. The pieces of fabric are then conditioned in a sealed container over silica gel for 30 minutes and subsequently subjected to the actual flameproofing test in a combustion chamber. The pieces of fabric are each ignited with a methane gas flame for 3 seconds in the vertical position. The test is considered as having been passed if the average charred zone is not more than 17.5 cm in length and no single sample exhibits a carred zone of over 25.4 cm in length and the individual smouldering times are not longer than 10 seconds.

EXAMPLE 12

The procedure as described in Example 11 is followed, except that the products of the formulae (10.1) to (10.7) are used. The results are summarised in the following Table II.

Table II

| Constituents Conditions | un-trea-ted | Treated with liquor | | | | | | |
|---|---|---|---|---|---|---|---|---|
| | | 1 | 2 | 3 | 4 | 5 | 6 | 7 |
| g of product of the formula (10.1) per kg of liquor | | 231 | | | | | | |
| g of product of the formula (10.2) per kg of liquor | | | 231 | | | | | |
| g of product of the formula (10.3) per kg of liquor | | | | 231 | | | | |
| g of product of the formula (10.4) per kg of liquor | | | | | 231 | | | |
| g of product of the formula (10.5) per kg of liquor | | | | | | 231 | | |
| g of product of the formula (10.6) per kg of liquor | | | | | | | 231 | |
| g of product of the formula (10.7) per kg of liquor | | | | | | | | 231 |
| solvent | | ethanol | methanol | methanol | methanol | methanol | methanol | methanol |
| liquor pick-up (%) | | 65 | 65 | 65 | 65 | 65 | 65 | 65 |
| thermosol treatment temperature ° C | | 200 | 200 | 200 | 200 | 200 | 200 | 200 |
| thermosol treatment time in secs. | | 60 | 20 | 20 | 20 | 20 | 20 | 20 |
| deposit after final wash (%) | | 11.5 | 14.3 | 15.0 | 14.0 | 11.3 | 11.5 | 12.6 |
| Flame resistance (ignition time in secs/tear length in cm) | | | | | | | | |
| before thermosol treatment | 17/9.5 | | | | | | | |
| after final wash | burns | 9.7 | 2/7 | 0/6.5 | 0/7 | 0/7.5 | 0/7.5 | 0/7.5 |
| after 25 washes | burns | 13/7.5 | 1/5.5 | 2/6 | 0/5.5 | 1/6 | 2/5.5 | 2/6.5 |
| after 50 washes | burns | — | 0/5.5 | 1/6 | 1/6 | 3/5.5 | 4/6.6 | 4/5.5 |

EXAMPLE 13

A 12.5% solution of polyester (polyethylene glycol terephthalate) in hexafluoroisopropanol is treated with one of the phosphates of the formulae (9), (10.5), (10.8) or (10.9) and applied to a glass plate so as to produced a layer thickness of about 0.5 mm. A glass fibre fabric is then placed on this layer and gentle pressure is applied. A second portion of the above solution is next applied in a layer having a thickness of about 0.5 mm to the glass fibre fabric so that a total layer thickness of 1 mm is obtained. The hexafluoroisopropanol is evaporated at 100° C and 20 Torr to give glass reinforced polyester cast films. The amount of the phosphates used in the casting solution is so measured that the films contain in each case 5% or 10% of the phosphates. The polyester cast films are tested for their flame resistance by measuring the Limiting Oxygen Index (LOI). Simultaneously, a polyester film which has been prepared without addition of phosphate is tested. The test for measuring the LOI is carried out in the manner described in Modern Plastics, pp. 141, 142, 146, 148 and 192, November 1966. LOI values of 0.21 and above characterise materials which no longer burn after they have been ignited in air. The results are summarised in the following Table III.

Table III

| Phosphate used corresponding to the formula | Content of phosphate in the film (%) | LOI |
| --- | --- | --- |
| (9) | 5 | 0.228 |
| (9) | 10 | 0.251 |
| (10.5) | 5 | 0.218 |
| (10.5) | 10 | 0.244 |
| (10.8) | 5 | 0.215 |
| (10.8) | 10 | 0.240 |
| (10.9) | 5 | 0.223 |
| (10.9) | 10 | 0.239 |
| without phosphate | 0 | 0.191 |

The LOI values of Table III show that the test samples made with the addition of a phosphate according to the invention are unable to burn in the air after they have been ignited in contrast to test samples which are made without addition of a phosphate.

EXAMPLE 14

A polyurethane soft foam is prepared by mixing the following materials: 100 g of a polyhydroxyl compound of a polyether suitable for polyurethane soft foam formation and having a molecular weight of about 3000 (manufactured from trimethylol propane and propylene oxide),
1 g of siloxane-oxyalkylene copolymer,
0.32 g of tin(II)-octoate (catalyst),
3.5 g of water,
48.2 g of toluylene diisocyanate (80:20 mixture of 2,4/2,6-isomers),
6 g of the phosphate according to formula (10.8).

The resulting polyurethane soft foam is tested for its flame resistance according to ASTM D 1692 test method, the test being repeated after the test samples have been stored for 7 days at 140° C in a dry atmosphere and at 90° C in a humid atmosphere as well as after 5 hours storage at 120° C in an atmosphere saturated with steam. Simultaneously, a polyurethane soft foam specimen which was manufactured without addition of a phosphate is also tested. The results are summarised in the following Table IV.

Table IV
Flame resistance of polyurethane soft foam test samples according to ASTM D 1692 test BZ = burned zone in cm/RC = rate of combustion in CM/min.

| | without storage | after 7 days storage at 140° C (dry) | after 7 days storage at 90° C (humid) | after storage at 120° C (saturated steam) in hours |
| --- | --- | --- | --- | --- |
| test samples with phosphate added BZ/RC | 7.5/9.3 | 5.0/12.8 | 9.5/10.7 | 8.5/10.3 |
| test samples without phosphates | burned through/27 | burned through/19 | burned through/17 | burned through/18 |

ASTM D 1692 Test

One each of the test samples measuring 150 mm × 50 mm × 13 mm is fixed with the 50 mm × 13 mm edge in the horizontal position. Markings are made at 24 mm and 100 mm. The sample is ignited at its bottom end with a dovetail burner. The ignition time is 60 seconds. If the burned zone is not longer than 25 mm, the foam is termed non-inflammable. If the sample burned over the 25 mm mark and the burned zone is smaller than 125 mm, the foam is termed self-extinguishing. The length of the burned zone is indicated in centimeters. If the sample burns over the 125 mm mark, the foam is termed inflammable and the rate of combustion is indicated.

We claim:

1. A process for flameproofing organic fiber material, which comprises applying to said material a preparation which contains a phosphate of the formula

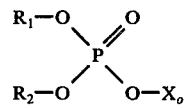

wherein each of $R_1$ and $R_2$ is bromoalkyl with 2 to 6 carbon atoms and $X_o$ is unsubstituted phenyl, phenyl which is substituted in ortho- or para-position by phenyl, monoalkylphenyl or dialkylphenyl with 1 to 9 carbon atoms in each alkyl moiety; drying the material and subjecting it to a heat treatment at 175° to 220° C. for about 10 to 200 seconds.

2. A process according to claim 1, which comprises applying a preparation which contains a phosphate of the formula

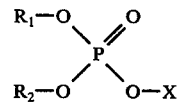

wherein each of $R_1$ and $R_2$ is bromoalkyl with 2 to 6 carbon atoms and X is phenyl, monoalkylphenyl or dialkylphenyl with 1 to 9 carbon atoms in each alkyl moiety.

3. A process according to claim 1, which comprises applying a preparation which contains a phosphate of the formula

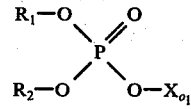

wherein $X_{o_1}$ is phenyl, alkylphenyl with 1 to 9 carbon atoms in the alkyl moiety, 2- or 4-diphenylyl them in claim 1.

4. A process according to claim 1, which comprises applying a preparation which contains a phosphate of the formula

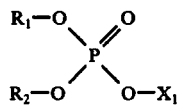

wherein $X_1$ is phenyl, alkylphenyl with 1 to 9 carbon atoms in the alkyl moiety, 4-diphenylyl and $R_1$ and $R_2$ have the meanings assigned to them in claim 1.

5. A process according to claim 1 wherein $R_1$ and $R_2$ each have the same meaning.

6. A process according to claim 1, which comprises applying a preparation which contains a phosphate of the formula

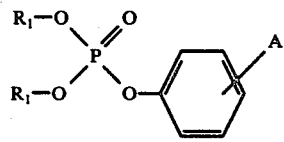

wherein A is hydrogen or alkyl with 1 to 9 carbon atoms and $R_1$ has the meaning assigned to it in claim 1.

7. A process according to claim 1, which comprises applying a preparation which contains a phosphate of the formula

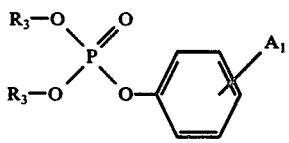

wherein $R_3$ is dibromopropyl and $A_1$ is hydrogen or methyl.

8. A process according to claim 1, which comprises applying a preparation which contains the phosphate of the formula

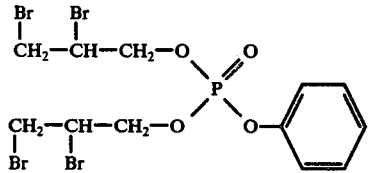

9. A process according to claim 1, which comprises applying a preparation which contains the phosphate of the formula

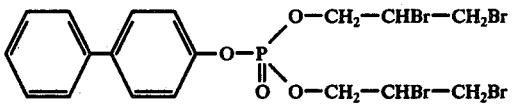

10. A process according to claim 1, which comprises applying a preparation which contains the phosphate of the formula

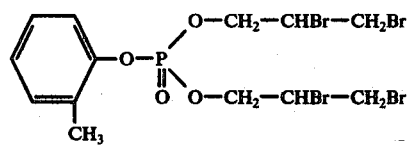

11. A process according to claim 1, which comprises applying a preparation which contains the phosphate of the formula

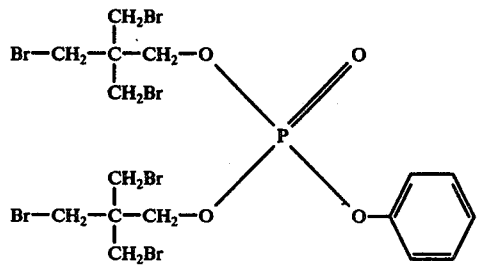

12. A process according to claim 1, which comprises applying a preparation which contains the phosphate of the formula

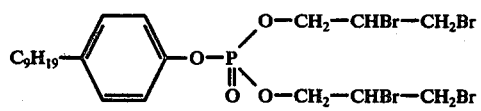

13. A process according to claim 1, which comprises applying a preparation consisting of an aqueous emulsion or suspension.

14. A process according to claim 1, which comprises applying a preparation consisting of an organic solution of aliphatic alcohols or chlorinated hydrocarbons with 1 to 4 carbon atoms.

15. A process according to claim 1, which comprises flameproofing polyester fibers as organic fiber material.

* * * * *

UNITED STATES PATENT OFFICE
CERTIFICATE OF CORRECTION

Patent No. 4,055,689  Dated October 25, 1977

Inventor(s) HERMANN NACHBUR ET AL

It is certified that error appears in the above-identified patent and that said Letters Patent are hereby corrected as shown below:

In claim 3, column 16, line 64, after "4-diphenyl", insert -- and $R_1$ and $R_2$ have the meanings assigned to --.

Signed and Sealed this

Fifteenth Day of August 1978

[SEAL]

Attest:

RUTH C. MASON
Attesting Officer

DONALD W. BANNER
Commissioner of Patents and Trademarks